United States Patent
Canto et al.

(10) Patent No.: US 7,776,807 B2
(45) Date of Patent: Aug. 17, 2010

(54) LIQUID CLEANSING COMPOSITIONS COMPRISING MICROFIBROUS CELLULOSE SUSPENDING POLYMERS

(75) Inventors: Cristiane Aparecida F. Canto, Campinas (BR); Chandra Shekar Palla Venkata, Hamden, CT (US); Yuntao Thomas Hu, Orange, CT (US); Prabhjyot Singh, Stratford, CT (US); Lin Yang, Woodbridge, CT (US); Martin Swanson Vethamuthu, Southbury, CT (US); Alexander Lips, Bebington (GB)

(73) Assignee: Conopco, Inc., Englewood Cliffs, NJ (US)

(*) Notice: Subject to any disclaimer, the term of this patent is extended or adjusted under 35 U.S.C. 154(b) by 0 days.

(21) Appl. No.: 12/218,088

(22) Filed: Jul. 11, 2008

(65) Prior Publication Data

US 2010/0009891 A1   Jan. 14, 2010

(51) Int. Cl.
  C11D 3/22 (2006.01)
  C11D 1/02 (2006.01)
  A61K 8/73 (2006.01)

(52) U.S. Cl. .............. 510/151; 510/121; 510/153; 510/159; 510/405; 510/437; 510/473; 510/475; 510/490; 510/492; 424/70.21; 424/70.22

(58) Field of Classification Search .......... 510/121, 510/151, 153, 159, 405, 437, 473, 475, 490, 510/492; 424/70.21, 70.22
See application file for complete search history.

(56) References Cited

U.S. PATENT DOCUMENTS

2008/0108714 A1* 5/2008 Swazey et al. ............. 516/31
2008/0146485 A1* 6/2008 Swazey ...................... 510/446

FOREIGN PATENT DOCUMENTS

WO    WO 2009/101545    * 8/2009

OTHER PUBLICATIONS

"Microbial Cellulose: A New Resource for Wood, Paper, Textile, Food and Specialty Products", by R.M. Brown Jr., (http://www.botany.utexas.edu/facstaff/facpages/mbrown/position1.htm), Feb. 6, 2008.

* cited by examiner

*Primary Examiner*—Brian P Mruk
(74) *Attorney, Agent, or Firm*—Ronald A. Koatz

(57) ABSTRACT

The present invention relates to personal care liquid cleansing compositions comprising bacterially produced microfibrous cellulose (MFC) suspending polymers which have not previously been used in personal care compositions.

7 Claims, 2 Drawing Sheets

SCHEMATIC MODEL OF PLANT (LEFT)
AND BACTERIAL (RIGHT) CELLULOSE FIBRILS

LIQUID CLEANSING COMPOSITIONS COMPRISING MICROFIBROUS CELLULOSE SUSPENDING POLYMERS

FIELD OF THE INVENTION

The present invention relates to liquid cleanser compositions (e.g., personal care liquid cleaners) including cleansers comprising 0.5-40%, preferably 0.5-25%, even more preferably 5 to 18% by wt. surfactant. In particular it relates to compositions in which, when microfibrous cellulose is used as suspending polymer, quite surprisingly, reduced levels of the polymer (e.g., 0.01 to 1.0% by wt.) can be used while enhancing the suspension efficiency (i.e., less polymer suspends same or more) of the polymer. Further, this is done without affecting rheological properties (e.g., high zero shear viscosity and low high shear viscosity). In addition, higher levels of salt (which helps structure surfactant) surprisingly do not affect the ability of the microfibrous cellulose polymer to efficiently structure (i.e., compositions are salt tolerant to instability).

BACKGROUND

Personal care compositions which can suspend beads and/or other particles are very desirable. The suspended materials can add a number of beneficial uses which include, but are certainly not limited to: abrasion, visual impact (e.g., optical particles), encapsulates.

Typically, particles are suspended in personal care compositions using structuring systems such as acrylate polymers, structuring gums (e.g., xanthan gum), starch, agar, hydroxyl alkyl cellulose, etc. When large particles are suspended (e.g., polyethylene particles, guar beads etc.), the level of polymer used is typically 1% or more. These high polymer levels increase the cost of the formulation, and it would be desirable to find suspending polymers which suspend, even when used in smaller amounts.

Applicants have now found suspending polymers which, when used in the personal care liquid compositions of the invention, quite unpredictably provide tremendous structuring efficiency (e.g., suspend high amount of beads, particles, etc., even relatively large size particles, at low levels of polymer); provide excellent rheological properties (e.g., high zero or low shear viscosity and low high shear viscosity); and are salt tolerant, if salt is used in the formulation.

More specifically, the microfibrous cellulose of the invention provides excellent suspending properties when used at low levels (0.01-1%, preferably 0.02-0.5% by wt.) for suspending particles as large as 3000 microns; of course it can be used at even lower levels to suspend smaller particles (1-1000, preferably 1-800 microns).

In particular, the microfibrous cellulose can be used in compositions with 0.5-40% surfactant where, whether low or high amounts of surfactant are used to provide structuring/suspension ability, small amounts of suspending polymer of the invention can be used. A further benefit is that, in the presence of salt (added to help the surfactant structure, for example, to form rod-like to worm-like micelles and therefore enhance structure/suspension even further), the suspending polymer does not lose its suspending effect. This contrasts with many other suspending polymers which tend to be salt intolerant and lose suspending powers. In addition the polymer can be used to form transparent liquid compositions.

In general, cellulose is an organic compound with formula $(C_6H_{10}O_5)_n$. It is a structural polysaccharide derived from beta glucose and is the primary structural component of green plants.

Traditionally, cellulose is harvested from plant resources (e.g., cotton, wood). The cellulose is assembled from glucose, which glucose is produced in the living plant cell from photosynthesis. Cellulose may also be made by photosynthetic plant microbes, such as unicellular plankton or algae found in the ocean.

Cellulose can also be assembled by bacteria. However, the bacteria is typically devoid of photosynthetic capacity and usually requires glucose or organic substrate synthesized by a photosynthetic organism to assemble cellulose. Some bacteria can use methane or sulfur substrates to produce glucose and other organic substrates for cellulose (see "Microbial Cellulose: A New resource for Wood, Paper, Textile, Food and Specialty Products", by R. M. Brown Jr., (http://www-.botany.utexas.edu/facstaff/facpages/mbrown/position1.htm)

One bacteria for example, Acetobacter xylinum, is a non-photosynthetic organism which can procure glucose sugar etc. and convert into cellulose. As noted in the reference cited, a cell of acetobacter has a linear row of pores from which glucan chain polymer aggregates are spun. The pores can produce a cable of polymers resulting in cellulose "ribbons" and these are spun into fibrils.

These type of bacterially produced microfibrous cellulose polymers, as noted in the reference to Brown, Jr., have been contemplated for use in industries including the food industry and healthcare. It is also noted from the reference that the polymers could be used for skin creams.

Nowhere that applicants are aware, however, have these type of polymers been contemplated for use in personal wash liquid cleanser compositions. Nor would it be predictable that these polymers would have such tremendous suspension ability when used in personal wash liquid cleanser.

Unexpectedly and quite unpredictably, however, applicants have now found that microfibrous cellulose can be used in small amount (e.g., 0.01 to 1.0%, preferably 0.1-0.5% by wt.) to suspend, for example, capsules, particles, air bubbles, from 1-3000µ in size, while maintaining desired rheological properties (i.e., high zero shear viscosity, as required for suspending and low high shear viscosity as required for ready pourability). Further these unbelievably efficient polymers are salt tolerant (while not wishing to be bound by theory, this is believed to be true because the polymers are nonionic), and can be used for preparing transparent compositions.

BRIEF SUMMARY OF THE INVENTION

Specifically the present invention relates to liquid cleanser compositions comprising:
 (1) 0.5 to 40%, preferably 0.5 to 25% by wt. surfactant selected from the group consisting of anionic, nonionic, amphoteric/zwitterionic, cationic surfactant and mixtures thereof (preferably there should be at least some anionic surfactant and anionic should comprise 50% or greater of the surfactant system);
 (2) 0 to 25% by wt. optional thickener;
 (3) 0 to 15% by wt., preferably 0.1-5% by wt. of a moisturizing compound (also may reduce viscosity) selected from the group consisting of glycerin, polyalkylene glycol and mixtures thereof;

(4) 0.01 to 2%, preferably 0.01 to 1%, more preferably 0.05 to 0.8%, more preferably 0.05 to ≦0.5% by wt. microfibrous cellulose, particularly bacterially produced cellulose (5) suspended particles (e.g., optical particles, capsules, air bubbles) having particle size of 1-3000 microns; and (6) 20 to 98%, preferably 40 to 98% by w. water.

wherein zero shear viscosity varies from 100 to 10,000,000 ($10^2$ to $10^7$), preferably 1,000 to 9,000,000 Pa·s, and high shear viscosity (measured at shear rate of 0.1 to 10 1/s at 23° C.) varies from 1 to 50,000 mPa·s.

In some embodiments, the compositions may be isotropic. Compositions may be transparent (clear), although pearlizer can be added.

In another embodiment, the compositions may comprise 0.1-3%, preferably 0.1-1% by wt. salt while retaining stability (e.g., will not phase separate after 2 wks stored at room temperature or even when stored for two (2) weeks at 45° C.). Preferred salts include alkali metal chlorides such as sodium or magnesium chloride. Typically, salt is used for products with particularly low levels of microfibrous cellulose and/or surfactant to build up high shear viscosity.

Although the compositions may comprise 0.5-40% surfactant (i.e., concentrate or non-concentrate compositions), preferred compositions are low-active (e.g., 20% by wt. or less, preferably 12% by wt. or less, more preferably 1-10% by wt. surfactant) compositions. It is in such low active compositions (where there is little surfactant to assist in structuring) that it is particularly remarkable that low amounts of the bacterially produced microfibrous cellulose can have the effects noted, especially compared to other structuring polymers.

In one embodiment, the compositions are isotropic liquids, by which is typically meant clear or transparent, and comprise 1-25% by wt. anionic (e.g., alkyl ether sulfate, glycinate) and 1-15% by wt. amphoteric surfactant (e.g., betaine). Whether the composition is isotropic depends to some extent also on the pH of the formulation.

In another embodiment, the compositions are lamellar liquids comprising 1 to 40% by wt. anionic surfactant and 0.5 to 20% by wt. of a lamellar phase inducing compound selected from, for example, fatty acids, fatty alcohols, etc. In another preferred embodiment, the composition comprises 0.5 to 40% DEFI surfactant.

These and other aspects, features and advantages will become apparent to those of ordinary skill in the art from a reading of the following detailed description and the appended claims. For the avoidance of doubt, any feature of one aspect of the present invention may be utilized in any other aspect of the invention. It is noted that the examples given in the description below are intended to clarify the invention and are not intended to limit the invention to those examples per se. Other than in the experimental examples, or where otherwise indicated, all numbers expressing quantities of ingredients or reaction conditions used herein are to be understood as modified in all instances by the term "about". Similarly, all percentages are weight/weight percentages of the total composition unless otherwise indicated. Numerical ranges expressed in the format "from x to y" are understood to include x and y. When for a specific feature multiple preferred ranges are described in the format "from x to y", it is understood that all ranges combining the different endpoints are also contemplated. Where the term "comprising" is used in the specification or claims, it is not intended to exclude any terms, steps or features not specifically recited. All temperatures are in degrees Celsius (° C.) unless specified otherwise.

All measurements are in SI units unless specified otherwise. All documents cited are—in relevant part—incorporated herein by reference.

DETAILED DESCRIPTION OF INVENTION

Figure 1:
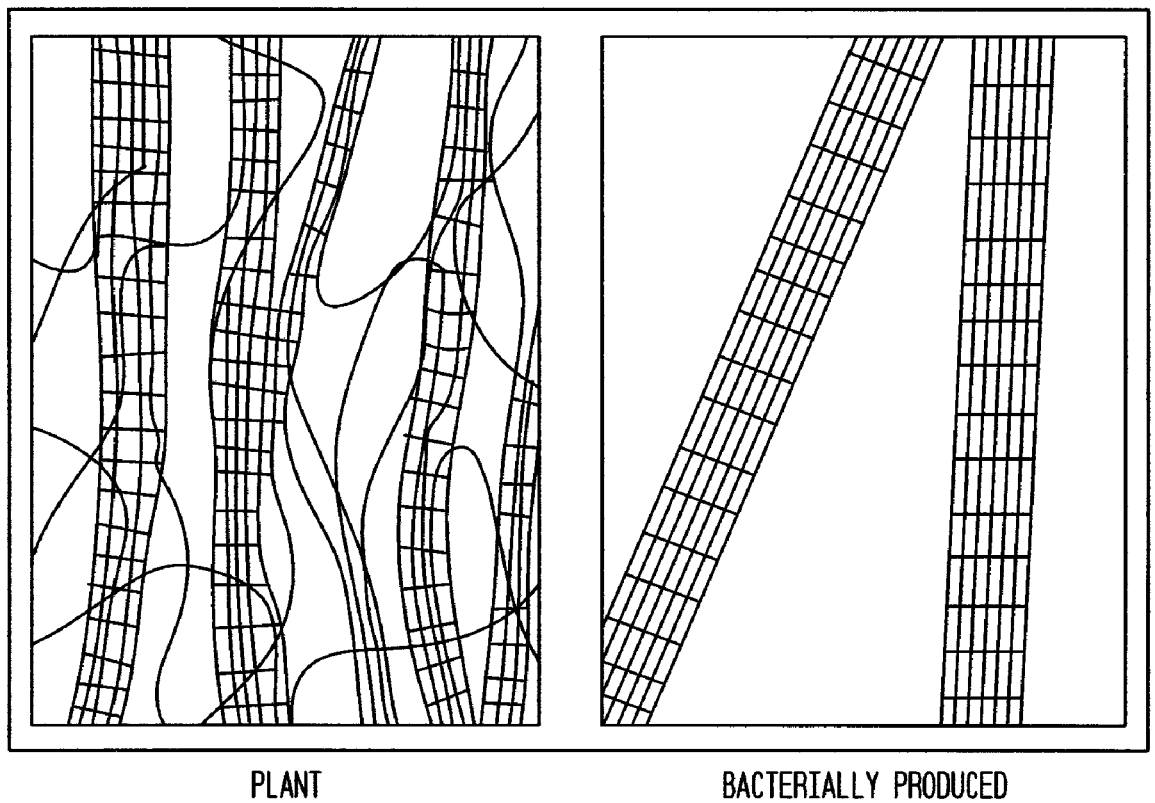
FIG. 1 is a schematic model of plant (left) and bacterial (right) cellulose fibrils.

The present invention relates to liquid cleanser compositions comprising bacterially produced microfibrous cellulose. These bacterially produced cellulose have unexpected properties when used in liquid cleanser compositions (e.g., because of fiber-like geometry with aspect ratio of greater than 1, that is length greater than width) which allows reduced amounts to be used while providing same suspension benefits relative to other suspending polymers used in liquid cleanser compositions, all while maintaining desirable rheology (e.g., excellent high and low shear viscosities).

Typically, the compositions of the invention are isotropic (e.g., clear) liquid compositions (although they may be lamellar) comprising about 0.5 to 40%, preferably 0.5 to 25% by wt. of a surfactant system. As noted, it is possible for the compositions to comprise enough lamellar inducing component (e.g.; fatty acids or fatty alcohols) to be in lamellar phase.

The compositions are used to suspend particles which may be up to 3000 microns in size. Among particles which may be suspended (illustrative only) are beads (e.g., glass beads, plastic beads), insoluble dimethicones, organic or inorganic materials, crystalline solids, oil droplets, air and gas bubbles etc.

In one embodiment, the suspending polymers (e.g., microfibrous cellulose (MFC)) may be put to particularly efficient use in low active systems comprising 15% by wt. or less, preferably 5 to 12% by wt. surfactant. Whether in higher or lower active system, at least some anionic should preferably be present and such should preferably comprise 50% or greater, preferably 60% or greater of the surfactant system (which preferably is and anionic and zwitterionic surfactant system).

The compositions optionally may comprise a thickener (0-25% thickener for higher active compositions, i.e., compositions with 10-40% by wt. surfactant; and 0-5%, preferably 0.1-3% by wt. for low active compositions).

The compositions may comprise 0-15%, preferably 0.1 to 5% by wt. of a moisturizing compound such as glycerin, polyalkylene glycol or a mixture thereof.

Compositions will also comprise water and other components found in liquid cleanser compositions as described in greater detail below.

Surfactants

The compositions of the invention may comprise from 0.5-40% by wt. of a surfactant selected from the group consisting of anionic, non ionic amphoteric/zwitterionic and cationic surfactants and mixtures thereof. It is preferred that there should be at least some anionic surfactant and that anionic comprise at least 5% of the surfactant system.

In one embodiment, the compositions are low active surfactant compositions comprising 0.5 to 15% by wt., preferably 3 to 12% or less surfactant with some preference that at least some of surfactant be anionic and that anionic comprise at least 50% (at least half) of the surfactant system.

The anionic detergent active which may be used may be aliphatic sulfonates, such as a primary alkane (e.g., $C_8$-$C_{22}$) sulfonate, primary alkane (e.g., $C_8$-$C_{22}$) disulfonate, $C_8$-$C_{22}$ alkene sulfonate, $C_8$-$C_{22}$ hydroxyalkane sulfonate or alkyl glyceryl ether sulfonate (AGS); or aromatic sulfonates such as alkyl benzene sulfonate.

The anionic may also be an alkyl sulfate (e.g., $C_{12}$-$C_{18}$ alkyl sulfate) or alkyl ether sulfate (including alkyl glyceryl ether sulfates). Among the alkyl ether sulfates are those having the formula:

RO(CH$_2$CH$_2$O)$_n$SO$_3$M wherein R is an alkyl or alkenyl having 8 to 18 carbons, preferably 12 to 18 carbons, n has an average value of greater than 1.0, preferably greater than 3; and M is a solubilizing cation such as sodium, potassium, ammonium or substituted ammonium. Ammonium and sodium lauryl ether sulfates are preferred anionic; preferably they comprise 3 to 10% of the overall of the composition.

The anionic may also be alkyl sulfosuccinates (including mono- and dialkyl, e.g., $C_6$-$C_{22}$ sulfosuccinates); alkyl and acyl taurates, alkyl and acyl sarcosinates, sulfoacetates, $C_8$-$C_{22}$ alkyl phosphates and phosphates, alkyl phosphate esters and alkoxyl alkyl phosphate esters, acyl lactates, $C_8$-$C_{22}$ monoalkyl succinates and maleates, sulphoacetates, alkyl glucosides and acyl isethionates, and the like.

Sulfosuccinates may be monoalkyl sulfosuccinates having the formula:

R$^4$O$_2$CCH$_2$CH(SO$_3$M)CO$_2$M; and amide-MEA sulfosuccinates of the formula;

R$^4$CONHCH$_2$CH$_2$O$_2$CCH$_2$CH(SO$_3$M)CO$_2$M wherein R$^4$ ranges from $C_8$-$C_{22}$ alkyl and M is a solubilizing cation.

Sarcosinates are generally indicated by the formula:

R$^1$CON(CH$_3$)CH$_2$CO$_2$M, wherein R$^1$ ranges from $C_8$-$C_{20}$ alkyl and M is a solubilizing cation.

Taurates are generally identified by formula:

R$^2$CONR$^3$CH$_2$CH$_2$SO$_3$M wherein R$^2$ ranges from $C_8$-$C_{20}$ alkyl, R$^3$ ranges from $C_1$-$C_4$ alkyl and M is a solubilizing cation.

The inventive cleansing composition may contain $C_8$-$C_{18}$ acyl isethionates. These esters are prepared by reaction between alkali metal isethionate with mixed aliphatic fatty acids having from 6 to 18 carbon atoms and an iodine value of less than 20. At least 75% of the mixed fatty acids have from 12 to 18 carbon atoms and up to 25% have from 6 to 10 carbon atoms.

One or more amphoteric surfactants may be used in this invention. Amphoteric surfactants are preferably used at levels as low as about 0.5 or 0.8, and at levels as high as about 10% by wt. (proportionally lower in low active systems). Such surfactants include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

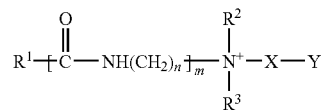

where R$^1$ is alkyl or alkenyl of 7 to 18 carbon atoms;
R$^2$ and R$^3$ are each independently alkyl, hydroxyalkyl or carboxyalkyl of 1 to 3 carbon atoms;
n is 2 to 4;
m is 0 to 1;
X is alkylene of 1 to 3 carbon atoms optionally substituted with hydroxyl, and
Y is —CO$_2$— or —SO$_3$—

Suitable amphoteric surfactants within the above general formula include simple betaines of formula:

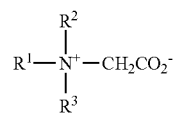

and amido betaines of formula:

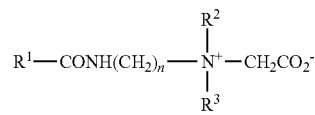

where n is 2 or 3.

In both formulae R$^1$, R$^2$ and R$^3$ are as defined previously. R$^1$ may in particular be a mixture of $C_{12}$ and $C_{14}$ alkyl groups derived from coconut oil so that at least half, preferably at least three quarters of the groups R$^1$ have 10 to 14 carbon atoms. R$^2$ and R$^3$ are preferably methyl.

A further possibility is that the amphoteric detergent is a sulphobetaine of formula:

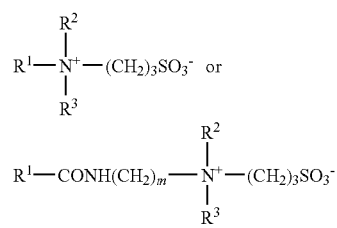

where m is 2 or 3, or variants of these in which —(CH$_2$)$_3$SO$_3$— is replaced by

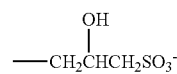

In these formulae R$^1$, R$^2$ and R$^3$ are as discussed previously.

A preferred surfactant system of the invention is one comprising 5-10% by wt. alkali metal ether sulfate and 1-5%, preferably 2-4% by wt. cocoamidoalkyl sultaine (e.g., cocoamidohydroxy propyl sultaine).

Amphoacetates and diamphoacetates are also intended to be covered in possible zwitterionic and/or amphoteric compounds which may be used such as e.g., sodium lauroamphoacetate, sodium cocoamphoacetate, and blends thereof, and the like.

The nonionics which may be used include in particular the reaction products of compounds having a hydrophobic group and a reactive hydrogen atom, for example aliphatic alcohols, acids, amides or alkylphenols with alkylene oxides, especially ethylene oxide either alone or with propylene oxide. Specific nonionic detergent compounds are alkyl ($C_6$-$C_{22}$) phenols ethylene oxide condensates, the condensation products of aliphatic ($C_8$-$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxide, and the like.

The nonionic may also be a sugar amide, such as a polysaccharide amide. Specifically, the surfactant may be one of the lactobionamides described in U.S. Pat. No. 5,389,279 to Au et al. titled "Compositions Comprising Nonionic Glycolipid Surfactants issued Feb. 14, 1995; which is hereby incorporated by reference or it may be one of the sugar amides described in U.S. Pat. No. 5,009,814 to Kelkenberg, titled "Use of N-Poly Hydroxyalkyl Fatty Acid Amides as Thickening Agents for Liquid Aqueous Surfactant Systems" issued Apr. 23, 1991; hereby incorporated into the subject application by reference.

One or more cationic surfactants may also be used in the cleansing composition. Cationic surfactants may be used at levels as low as about 0.1, 0.3, 0.5 or 1 and at levels as high as 2, 3, 4 or 5% by wt.

Examples of cationic detergents are the quaternary ammonium compounds such as alkyldimethylammonium halogenides.

Other suitable surfactants which may be used are described in U.S. Pat. No. 3,723,325 to Parran Jr. titled "Detergent Compositions Containing Particle Deposition Enhancing Agents" issued Mar. 27, 1973; and "Surface Active Agents and Detergents" (Vol. I & II) by Schwartz, Perry & Berch, both of which are also incorporated into the subject application by reference.

In a preferred embodiment, the surfactant system comprises both an alkyl ether sulfate (e.g., alkali-metal alkyl ether sulfate), at levels of about 2 to 20% and about 1-15% amphoteric (e.g., betaine such as cocoamidopropyl betaine or amidopropylsultaine).

The compositions may comprise 0-25%, preferably 0.5 to 10% by wt. of a thickening agent:

Suitable thickening agents can be added as a structurant for the composition. Suitable thickening agents include polyacrylates; fumed silica natural and synthetic waxes, alkyl silicone waxes such as behenyl silicone wax; aluminum silicate; lanolin derivatives such as lanesterol; C8 to C20 fatty alcohols; polyethylene copolymers; polyammonium stearate; sucrose esters; hydrophobic clays; petrolatum; hydrotalcites; and mixtures thereof, and the like.

Particularly preferred thickening agents include silica, alkyl silicone waxes, paraffin wax, C8 to C20 fatty alcohols, petroleum jelly and polyethylene copolymers, blends thereof and the like.

While some materials can function as both an emollient and a thickener therefore it will be appreciated that the emollient and thickening function cannot be provided by the same component. However, it will be understood that where the composition comprises two or more emollients one of said emollients could also function as a thickening agent.

Preferably the amount of thickening agent may be as low as about 1% by wt. and up to about 5, 10, 15, 20 or 25% by weight.

Although the compositions of the invention may be self-structuring, preferably they will also comprise a structurant, i.e. a material added to increase the viscosity at zero shear. Suitable materials include swelling clays, for example laponite; fatty acids and derivatives hereof and, in particular fatty acid monoglyceride polyglycol ethers; cross-linked polyacrylates such as Carbopol™ (polymers available from Goodrich); acrylates and copolymers thereof e.g. Aqua SF-1 available from Noveon (Cleveland, Ohio), polyvinylpyrrolidone and copolymers thereof; polyethylene imines; salts such as sodium chloride and ammonium sulphate; sucrose esters; gellants; natural gums including alginates, guar, xanthan and polysaccharide derivatives including carboxy methyl cellulose and hydroxypropyl guar; propylene glycols and propylene glycol oleates; glycerol tallowates; and mixtures thereof, mixtures thereof, and the like.

Of the clays particularly preferred are synthetic hectorite (laponite) clay used in conjunction with an electrolyte salt capable of causing the clay to thicken. Suitable electrolytes include alkali and alkaline earth salts such as halides, ammonium salts and sulphates, blends thereof and the like.

Further examples of structurants and thickeners are given in the International Cosmetic Ingredient Dictionary, Fifth Edition, 1993, published by CTFA (The Cosmetic, Toiletry & Fragrance Association), incorporated herein by reference.

In addition to whatever thickeners and/or structurants the compositions may optionally contain (some of which, as noted, may have dual functionality of thickener and emollient). The compositions may comprise 0-15%, preferably 0.1-5% by wt. of a moisturizing agent specifically selected form the group consisting of glycerin, polyalkylene glycol and mixture thereof. Preferably, the composition will comprise 0.1-5%, more preferably 0.5-3% glycerin.

A key and necessary component of the invention is microfibrous cellulose (MFC) which must be present (to structure and suspend), whether or not other thickeners and/or structurants and moisturizing agents (e.g., glycerin, acrylate copolymers) are present.

In general, cellulose is an insoluble polysaccharide made of repeating glucose units. It is conventionally derived from plants and typically comprises both amorphous and crystalline domains.

Typically, cellulose is produced through a non-microbial process. Typically, for example, microcrystalline cellulose (a highly crystalline particulate cellulose made primarily of crystalline aggregates) is obtained by removing amorphous fibrous cellulose regions of a purified cellulose source material by hydrolytic degradation. This is typically done with a strong mineral acid (e.g., hydrogen chloride). Such acid hydrolysis process produces a microcrystalline cellulose of predominantly coarse particulate aggregates, typically of mean size range 10 to 40 microns.

The microfibrous cellulose of the invention, rather than being plant derived and producing 10-40 micron aggregates as noted, is bacterially produced and results in fiber bundles 0.1 to 2.2 microns in diameter. A schematic of plant (left) compared bacterial (right) cellulosic fibrils is seen in FIG. 1.

Bacterial produced MFC may have advantages relative to use of plant cellulose in that it has higher aspect ratio (e.g., greater weight effectiveness) and can be produced far more quickly. The aspect ratio is at least greater than 1 (i.e., length to width ratio greater than 1).

Typically, the cellulose will form a three dimensional matrix when dispersed in water under shear.

The cellulose structurant of the invention can be used in amounts from 0.01 to 2.0%, preferably 0.01 to 1%, more preferably 0.01 to 0.5%. Typically, even at range of 0.01 to 0.25% by wt. all the suspension abilities and advantages (e.g., rheological) are still maintained.

Typically, the compositions of the invention are in isotropic micellar phase. Although they may be in lamellar phase, the attributes of MFC (for suspending) are most appreciated in non-lamellar compositions, particularly those of low active concentration.

The rheological behavior of all surfactant solutions, including liquid cleansing solutions, is strongly dependent on the microstructure, i.e., the shape and concentration of micelles or other self-assembled structures in solution.

When there is sufficient surfactant to form micelles (concentrations above the critical micelle concentration or CMC), for example, spherical, cylindrical (rod-like or discoidal), spherocylindrical, or ellipsoidal micelles may form. As surfactant concentration increases, ordered liquid crystalline phases such as lamellar phase, hexagonal phase, cubic phase or L3 sponge phase may form. The non-isotropic hexagonal phase, consists of long cylindrical micelles arranged in a hexagonal lattice. In general, the microstructure of most personal care products consist of either an isotropic dispersion including spherical micelles; and rod micelles; or an ordered liquid crystalline phase such as a lamellar dispersion.

As noted above, micelles may be spherical or rod-like. Formulations having spherical micelles tend to have a low viscosity and exhibit Newtonian shear behavior (i.e., viscosity stays constant as a function of shear rate; thus, if easy pouring of product is desired, the solution is less viscous). In these systems, the viscosity increases linearly with surfactant concentration.

Rod micellar solutions are more viscous because movement of the longer micelles is restricted. At a critical shear rate, the micelles align and the solution becomes shear thinning. Addition of salts increases the size of the rod micelles thereof increasing zero shear viscosity (i.e., viscosity when sitting in bottle) which helps suspend particles but also increases critical shear rate (point at which product becomes shear thinning; higher critical shear rates means that the product is more difficult to pour).

Lamellar dispersions differ from both spherical and rod-like micelles because they can have high zero shear viscosity (because of the close packed arrangement of constituent lamellar droplets), yet these solutions are very shear thinning (readily dispense on pouring). That is, the solutions can become thinner than rod micellar solutions at moderate shear rates.

In formulating liquid cleansing compositions, therefore, there is the choice of using isotropic micellar phases such as rod-micellar solutions; or lamellar dispersions. When rod-micellar solutions are used, they also often require the use of external structurants to enhance viscosity and to suspend particles. For this, carbomers and clays are often used. At higher shear rates (as in product dispensing, application of product to body, or rubbing with hands), since the rod-micellar solutions are less shear thinning, the viscosity of the solution stays high and the product can be stringy and thick.

Compositions of the invention, using the MFC structurant, have excellent rheological properties. This is seen in that, at zero shear viscosity (e.g., viscosity typically measured at shear rate of about $1\times10^{-5}$ 1/s) viscosity can range from 100 (e.g., for high surfactant compositions having about 12% surfactant) to up to 10 million (high viscosities, when seen, were using about 0.3 to 0.6% MFC) more preferably 1000 to up to 9 million, even more preferably 3000 to 6 million Pa·s. Typically, when using 0.01 to 0.25% MFC, viscosity is about 1000 to 2,000,000 and, at high MFC, upper viscosity is as high as 10 million Pa·s. This can be seen for FIG. 2.

Thus, it can be seen that zero or low shear viscosities (e.g., shear rate of $10^{-5}$ to $10^{-7}$ 1/s measured at 23° C. using rheometer noted above) are very high (excellent for suspension).

As importantly, high shear viscosity (e.g., shear rate of 0.1 to 100 1/s, measured in same way) is from about 1 to 50,000 mPa·s (i.e., $10^{-3}$ to 50 Pa·s), preferably 100 to 20,000 mPa·s. This is consistent with fact that the liquids can be readily poured.

The suspension polymers are remarkable in that they are able to suspend particles, e.g., particles of sizes from 1 to 3000 microns, even when used in small amounts and at much smaller amounts relative to the amount of different suspension polymers required to achieve the same results (see Table 5 below). Particles which are suspended include perfume encapsulates, polyethylene beads, mica, pearlizers, air, etc. and size can vary from 1 to 3000 micron.

Among particles which can be suspended include optical particles (e.g., $TiO_2$, mica), capsules (containing, for example, perfume or benefit agents such as oils or emollients), air, bubbles, etc. Typically, the particles may comprise 0.05 to 10%, preferably 0.1 to 5%, more preferably 0.1 to 3% of the composition.

The composition will typically comprise about 20 to 98% by wt., preferably 40 to 98% by wt. water.

Another important attribute is that bacterially made MFC of the invention is resistant to salt instability. Thus even at levels of 0.1-1% salt, the compositions are stable and maintain both high low shear viscosity and low high shear viscosity.

The pH of the compositions is typically about 6 to 8, preferably 6 to 7.

EXAMPLES

Examples 1-10 (Table 1) and 11-16 (Table 2) are all examples of MFC of invention used as structuring polymer (at concentrations ranging from 0.05 to 0.5% by wt,)

Examples 1-10 are set forth in the Table 1 below.

TABLE 1

| CHEMICAL NAME | 1 | 2 | 3 | 4 | 5 | 6 | 7 | 8 | 9 | 10 |
|---|---|---|---|---|---|---|---|---|---|---|
| Microfibrous cellulose | 0.05 | 0.2 | 0.5 | 0.10 | 0.2 | 0.5 | 0.2 | 0.5 | 0.1 | 0.2 |
| Cocamido propylhydroxy sultaine - CAPHS | 1.38 | 1.38 | 1.38 | 2.20 | 2.20 | 2.20 | 3.30 | 3.30 | 4.40 | 5.50 |
| SLES 1EO | 3.2 | 3.2 | 3.2 | 5.06 | 5.06 | 5.06 | 7.60 | 7.60 | 11.60 | 12.70 |
| CMEA | 0.43 | 0.43 | 0.43 | 0.74 | 0.74 | 0.74 | 1.10 | 1.10 |  | 1.80 |

TABLE 1-continued

| CHEMICAL NAME | 1 | 2 | 3 | 4 | 5 | 6 | 7 | 8 | 9 | 10 |
|---|---|---|---|---|---|---|---|---|---|---|
| Tetrassodium EDTA | 0.05 | 0.05 | 0.05 | 0.05 | 0.05 | 0.05 | 0.05 | 0.05 | 0.05 | 0.05 |
| Etidronic Acid | 0.02 | 0.02 | 0.02 | 0.02 | 0.02 | 0.02 | 0.02 | 0.02 | 0.02 | 0.02 |
| GLYCERIN | 1.00 | 1.00 | 1.00 | 1.00 | 1.00 | 1.00 | 1.00 | 1.00 | 1.00 | 1.00 |
| Guar-hdroxypropyltrimonium chloride | 0.20 | 0.20 | 0.20 | 0.20 | 0.20 | 0.20 | 0.20 | 0.20 | 0.20 | 0.20 |
| Methylchloroisothiazolinone Methylisothiazolinone | 0.0003 | 0.0003 | 0.0003 | 0.0003 | 0.0003 | 0.0003 | 0.0003 | 0.0003 | 0.0003 | 0.0003 |
| Perfume | 1.00 | 1.00 | 1.00 | 1.00 | 1.00 | 1.00 | 1.00 | 1.00 | 1.00 | 1.00 |
| MgCl2 | 1.00 | 0.75 | | 0.75 | 0.50 | | 0.20 | 0.10 | — | — |
| WATER | 91.67 | 91.77 | 92.22 | 88.88 | 89.03 | 89.23 | 85.33 | 85.13 | 81.63 | 77.53 |
| TOTAL | 100.00 | 100.00 | 100.00 | 100.00 | 100.00 | 100.00 | 100.00 | 100.00 | 100.00 | 100.00 |

Examples 1-10 in Table 1 above show liquid compositions comprising varying levels of surfactant (e.g., ranging from as low as 5.01% to 20% and MFC). All compositions have high low-shear viscosity (for good suspension) and low high shear viscosity (pourability). Compositions with lower surfactant and lower MFC concentration used some salt to help build up high shear viscosity.

Typically compositions were prepared as follows:

Preparation steps:
1) Add primary surfactant (typically anionic)+water
2) Add co-surfactants (such as CAPHS and/or cocoamidopropyl betaine)
3) Add cellulose
4) Add cationic (e.g., guar)
5) Add Glycerin
6) Add chealting agent (e.g., ethylene diaminetetraacetic acid (EDTA) and/or ethylenehydroxydiphosphonate (EHDP)) plus preservative (e.g., Kathon®)
7) Adjust pH to desired value (pH 4.0-8.0, preferably 6.0-7.5)

Examples 11-16 are set forth in Table 2 below:

TABLE 2

| CHEMICAL NAME | 11 | 12 | 13 | 14 | 15 | 16 |
|---|---|---|---|---|---|---|
| Microfibrous cellulose | 0.10 | 0.2 | 0.5 | 0.2 | 0.5 | 0.2 |
| Cocamido Propyl Betain - CAPB | 2.20 | 2.20 | 2.20 | 3.30 | 3.30 | 5.50 |
| SLES 1EO | 5.06 | 5.06 | 5.06 | 7.60 | 7.60 | 12.70 |
| CMEA | 0.74 | 0.74 | 0.74 | 1.10 | 1.10 | 1.80 |
| Tetrassodium EDTA | 0.05 | 0.05 | 0.05 | 0.05 | 0.05 | 0.05 |
| Etidronic Acid | 0.02 | 0.02 | 0.02 | 0.02 | 0.02 | 0.02 |
| GLYCERIN | 1.00 | 1.00 | 1.00 | 1.00 | 1.00 | 1.00 |
| Guar hydroxypropyltrimonium chloride | 0.20 | 0.20 | 0.20 | 0.20 | 0.20 | 0.20 |
| Methylchloroisothiazolinone Methylisothiazolinone (Kathon ®) | 0.0003 | 0.0003 | 0.0003 | 0.0003 | 0.0003 | 0.0003 |
| Perfume | 1.00 | 1.00 | 1.00 | 1.00 | 1.00 | 1.00 |
| Poly Propylene Glycol - PPG-9 | — | — | — | — | — | 0.20 |
| MgCl2 | 0.50 | 0.20 | | 0.20 | | |
| WATER | 89.13 | 89.33 | 89.23 | 85.33 | 85.23 | 77.33 |
| TOTAL | 100.00 | 100.00 | 100.00 | 100.00 | 100.00 | 100.00 |

Table 2 compositions were prepared the same as Examples 1-10 in Table 1. The compositions are similar except for slightly different surfactant concentrations.

The rheology data (low shear viscosity) (from Tables 3 and 5 and FIG. 2) show these examples have high suspending power (i.e., a high low shear viscosity is indicative of high suspending power).

Examples 17-22

Effects of Surfactant Concentration and Salt on Viscosity

Examples 17-22 are set forth in Table 3 below:

TABLE 3

| CHEMICAL NAME | 17 | 18 | 19 | 20 | 21 | 22 |
|---|---|---|---|---|---|---|
| Microfibrous cellulose | 0.10 | 0.10 | 0.20 | 0.20 | 0.15 | 0.15 |
| Cocamido propylhydroxy sultaine —CAPHS | 2.20 | 2.20 | 2.20 | 2.20 | 3.30 | 3.30 |
| SLES 1EO | 5.06 | 5.06 | 5.06 | 5.06 | 7.60 | 7.60 |
| CMEA | 0.74 | 0.74 | 0.74 | 0.74 | 1.10 | 1.10 |
| Tetrassodium EDTA | 0.05 | 0.05 | 0.05 | 0.05 | 0.05 | 0.05 |
| Etidronic Acid | 0.02 | 0.02 | 0.02 | 0.02 | 0.02 | 0.02 |
| GLYCERIN | 1.00 | 1.00 | 1.00 | 1.00 | 1.00 | 1.00 |
| Guar hydroxypropyltrimonium chloride | 0.20 | 0.20 | 0.20 | 0.20 | 0.20 | 0.20 |
| Methylchloroisothiazolinone Methylisothiazolinone | 0.0003 | 0.0003 | 0.0003 | 0.0003 | 0.0003 | 0.0003 |
| Perfume | 1.00 | 1.00 | 1.00 | 1.00 | 1.00 | 1.00 |
| Poly Propylene Glycol - PPG-9 | — | — | — | — | — | — |
| $MgCl_2$ | | 0.75 | | 0.50 | | 0.15 |
| WATER | 89.63 | 88.88 | 89.53 | 89.03 | 85.58 | 85.43 |
| Low shear viscosity (@ shear rate 1e−7 1/s) mPa·s | 3.88E+07 | 5.35E+07 | 4.23E+08 | 1.72E+08 | 2.81E+08 | 1.91E+08 |
| High shear Viscosity (@ shear rate 10 1/s) mPa·s | 8.90E+01 | 1.17E+03 | 1.89E+02 | 9.05E+02 | 5.15E+02 | 6.89E+02 |
| TOTAL | 100.00 | 100.00 | 100.00 | 100.00 | 100.00 | 100.00 |

Examples in Table 3 show the effect of polymer concentration, surfactant concentration and salt on the low and high shear viscosity. Normally, increase in polymer concentration enhances the low shear viscosity as indicated in examples 17, 19 and 21. Surfactant concentration and salt play a significant role in affecting the high shear viscosity. Examples 19 and 21 show the impact of surfactant concentration on high shear viscosity and examples 18, 20 and 22 show the effect of salt. Specifically, both concentration and salt increase high shear viscosity.

Example 23-28

Use of Different Surfactant Systems and of Higher Surfactant Cconcentrations

Examples 23-28 are set forth in Table 4 below:

TABLE 4

| CHEMICAL NAME | 23 | 24 | 25 | 26 | 27 | 28 |
|---|---|---|---|---|---|---|
| Microfibrous cellulose | 0.20 | 0.20 | 0.2 | 0.2 | 0.2 | 0.2 |
| Cocamido propylhydroxy sultaine - CAPHS | 4.00 | 4.00 | — | — | — | — |
| Cocamido Propyl Betain —CAPB | | | | | | 6.00 |
| SLES 1EO | | | | | 8.00 | 30.00 |
| Sodium Cocoyl Glycinate | 8.00 | 8.00 | 8.00 | 8.00 | | |
| Sodium Lauryl Amphoacetate | | | 4.00 | 4.00 | 4.00 | |
| Tetrassodium EDTA | 0.05 | 0.05 | 0.05 | 0.05 | 0.05 | 0.05 |
| Etidronic Acid | 0.02 | 0.02 | 0.02 | 0.02 | 0.02 | 0.02 |
| GLYCERIN | 1.00 | 1.00 | 1.00 | 1.00 | 1.00 | 1.00 |
| Guar hydroxypropyltrimonium chloride | 0.20 | 0.20 | 0.20 | 0.20 | 0.20 | 0.20 |
| Methylchloroisothiazolinone Methylisothiazolinone | 0.0003 | 0.0003 | 0.0003 | 0.0003 | 0.0003 | 0.0003 |
| Perfume | 1.00 | 1.00 | 1.00 | 1.00 | 1.00 | 1.00 |
| Poly Propylene Glycol - PPG-9 | — | — | — | — | — | 1.00 |
| $MgCl_2$ | | 0.25 | | 0.20 | 0.15 | |
| WATER | 85.53 | 85.28 | 85.53 | 85.33 | 85.38 | 60.53 |
| TOTAL | 100.00 | 100.00 | 100.00 | 100.00 | 100.00 | 100.00 |

Table 4 shows more examples of MFC structured products with different primary and cosurfactants. Example 28 is example of high surfactant concentration.

Examples 29-30 and Comparative A-F
Effect of MFC Relative to Other Structuring Polymers
Examples 29-30 and Comparative A-F are set forth in Table 5 below.

TABLE 5

| CHEMICAL NAME | 29 | 30 | Comp A | Comp B | Comp C | Comp D | Comp E | Comp F |
|---|---|---|---|---|---|---|---|---|
| Microfibrous cellulose | 0.2 | 0.5 | | | | | | |
| Acrylic polymer (aqua SF-1) | | | 0.2 | 0.5 | | | | |
| HEC | | | | | 0.2 | 0.5 | | |
| Starch | | | | | | | 0.2 | 0.5 |
| Cocamido propylhydroxy sultaine - CAPHS | 4.00 | 4.00 | 4.00 | 4.00 | 4.00 | 4.00 | 4.00 | 4.00 |
| SLES 1EO | 8.00 | 8.00 | 8.00 | 8.00 | 8.00 | 8.00 | 8.00 | 8.00 |
| CMEA | | | | | | | | |
| Tetrassodium EDTA | 0.05 | 0.05 | 0.05 | 0.05 | 0.05 | 0.05 | 0.05 | 0.05 |
| Etidronic Acid | 0.02 | 0.02 | 0.02 | 0.02 | 0.02 | 0.02 | 0.02 | 0.02 |
| GLYCERIN | 1.00 | 1.00 | 1.00 | 1.00 | 1.00 | 1.00 | 1.00 | 1.00 |
| Guar hydroxypropyltrimonium chloride | 0.20 | 0.20 | 0.20 | 0.20 | 0.20 | 0.20 | 0.20 | 0.20 |
| Methylchloroisothiazolinone Methylisothiazolinone | 0.0003 | 0.0003 | 0.0003 | 0.0003 | 0.0003 | 0.0003 | 0.0003 | 0.0003 |
| Perfume | 1.00 | 1.00 | 1.00 | 1.00 | 1.00 | 1.00 | 1.00 | 1.00 |
| WATER | 85.33 | 85.33 | 85.33 | 85.33 | 85.33 | 85.33 | 85.33 | 85.33 |
| Low shear viscosity (@ shear rate 1e−7 1/s) mPa·s | 4.23E+08 | 2.74E+09 | 6.67E+02 | 9.24E+07 | 1.32E+03 | 3.76E+06 | 5.20E+02 | 6.94E+02 |
| TOTAL | 100.00 | 100.00 | 100.00 | 100.00 | 100.00 | 100.00 | 100.00 | 100.00 |

Table 5 shows examples comparing different structuring polymers. At the same active levels, MFC is significantly better (see the low shear viscosity @ comparable polymer levels) than the acrylic based polymers, HEC (hydroxyethylcellulose) and starch. Note: starch particles in Comparatives E and F sediment with time.

Low shear and high shear viscosity data are obtained on MCR-300 (Paar-Physica) rheometer performing a steady rate sweep experiments. In our experiments, we used the cone and plate geometry with 50 mm radius and 2° cone angle. Measurements were at 23° C.

Example 31

Figure 2:
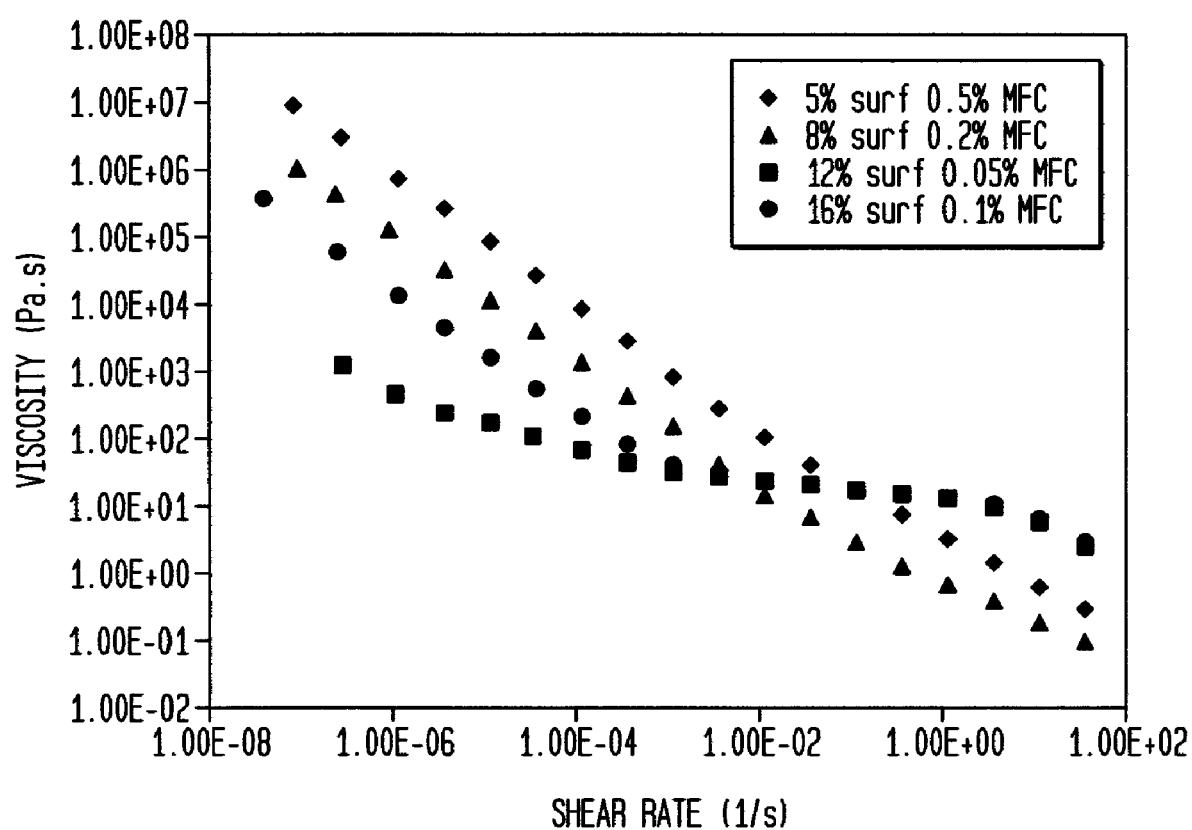
FIG. 2 is a graph showing high low shear viscosity and low high shear viscosity of compositions of the invention. It is remarkable that, using such small amounts of structuring polymer (MFC), such a profile of high low shear (for good suspensions) and low high shear (for pourability) viscosity can be observed.

As seen in FIG. 2, the compositions of the invention have both high low shear and low high shear viscosity

The invention claimed is:

1. Liquid composition consisting essentially of:
   (a) 1 to 10% by wt. surfactant wherein at least some of the surfactant is anionic, said anionic comprises at least 5% of the surfactant system, and anionic also comprises at least 50% of the total surfactant;
   (b) 0 to 25% by wt. thickener;
   (c) 0 to 15% by wt. of a moisturizing agent selected from the group consisting of glycerin, polyalkylene glycol and mixtures thereof;
   (d) 0.01 to 2% microfibrous cellulose;
   (e) 0.05 to 10%, 1-3000 micron particles; and
   (f) 20 to 98% by wt. water
   wherein said composition has high shear viscosity of 1 to 50,000 1/s at 23° C. mPa·s when measured at shear rate 0.1 to 100 1/s and wherein said composition comprises 0 to 0.5% salt while retaining low shear viscosity of at least 50,000
   wherein said composition is a low-active, isotropic, non-lamellar composition.

2. A composition according to claim 1, wherein surfactant comprises a combination of anionic and zwitterionic surfactant and anionic is in excess of zwitterionic.

3. A composition according to claim 1 comprising 0.1-5% by weight of a moisturizing agent selected from the group consisting of glycerin, polyalkylene glycol and mixtures thereof.

4. A composition according to claim 1 wherein the microfibrous cellulose is bacterially produced and comprises 0.01% to 1% by weight of the composition.

5. A composition according to claim 1 comprising 0.1 to 5% particles.

6. A composition according to claim 1, wherein particles are selected from the group consisting of optical particles, capsules, air bubbles and mixtures thereof.

7. A composition according to claim 1 having viscosity from 100 to 10,000,000 Pa·s when measured at shear rate $10^{-5}$ 1/s at 23° C.

* * * * *